(12) United States Patent
Grez

(10) Patent No.: US 7,857,623 B2
(45) Date of Patent: Dec. 28, 2010

(54) BRUSHHEAD STEM WITH CORE CHANNELS FOR DISPENSING FLUIDS

(75) Inventor: Joseph Grez, North Bend, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 77 days.

(21) Appl. No.: 10/582,659

(22) PCT Filed: Dec. 9, 2004

(86) PCT No.: PCT/IB2004/052822

§ 371 (c)(1),
(2), (4) Date: Apr. 24, 2007

(87) PCT Pub. No.: WO2005/058187

PCT Pub. Date: Jun. 30, 2005

(65) Prior Publication Data

US 2007/0212662 A1    Sep. 13, 2007

Related U.S. Application Data

(60) Provisional application No. 60/529,086, filed on Dec. 12, 2003.

(51) Int. Cl.
*A61C 17/00* (2006.01)
*A61C 3/02* (2006.01)
*A61C 5/04* (2006.01)
*A46B 13/00* (2006.01)

(52) U.S. Cl. ............................. 433/80; 433/88; 433/89; 15/22.1

(58) Field of Classification Search .................. 433/80, 433/87–89, 216; 15/22.1, 22.2; 401/146, 401/150, 135, 180, 151
See application file for complete search history.

(56) References Cited

U.S. PATENT DOCUMENTS

| 2,814,816 | A | | 12/1957 | Pepping et al. |
| 4,068,974 | A | * | 1/1978 | Meyer et al. ................. 401/150 |
| 4,236,651 | A | * | 12/1980 | Meyer et al. .................. 222/82 |
| 4,783,312 | A | * | 11/1988 | Gjertsen et al. ............. 376/458 |
| 5,096,321 | A | * | 3/1992 | Mountain .................... 401/149 |
| 6,039,489 | A | * | 3/2000 | Harman et al. .............. 401/146 |
| 6,164,967 | A | * | 12/2000 | Sale et al. ...................... 433/80 |
| 6,295,427 | B1 | * | 9/2001 | Flick et al. .................. 399/116 |
| 6,918,153 | B2 | * | 7/2005 | Gruber ........................ 15/22.1 |
| 2003/0077107 | A1 | * | 4/2003 | Kuo ............................ 401/278 |

FOREIGN PATENT DOCUMENTS

EP    0 385 815    9/1990

\* cited by examiner

*Primary Examiner*—Ralph A Lewis
*Assistant Examiner*—Yogesh Patel

(57) ABSTRACT

The stem portion of a toothbrush body has a set of bristles on a bristle plate at one end thereof, the stem portion including a shell or stem body having a longitudinal opening therethrough. A core member is configured to fit within the stem body, having two opposed grooves in the exterior surface thereof along the length thereof. The stem body has two grooves in the interior surface thereof, such that the grooves in the core member and the grooves in the stem body can align to form separate fluid channels along the length of the stem portion. The stem portion receives fluid from a reservoir and delivers the fluid to the bristle plate, which includes exit openings for the fluid. The core member and the stem body also include fluid-tight connections therebetween, separating the two channels.

11 Claims, 3 Drawing Sheets

BRUSHHEAD STEM WITH CORE CHANNELS FOR DISPENSING FLUIDS

CROSS REFERENCE TO RELATED APPLICATION

This application claims the benefit of U.S. provisional application Ser. No. 60/529,086 filed Dec. 12, 2003, which is incorporated herein whole by reference.

TECHNICAL FIELD

This invention relates generally to fluid-dispensing toothbrushes, and more specifically concerns a stem portion of a toothbrush with fluid channels extending therethrough.

BACKGROUND OF THE INVENTION

Fluid-dispensing toothbrushes typically include a tube or tubes or other fluid pathway which extend between a fluid reservoir, usually located in the handle of the toothbrush, to a brush plate which supports a field of bristles, where the fluid exits. The fluid-carrying tubes typically extend from the reservoir through a toothbrush stem portion of the toothbrush to the brush plate.

In many cases, the toothbrush stem will be molded as one piece and will include a channel extending longitudinally therethrough to accommodate the fluid flow, such as by a tube. In some cases, it is desirable to have more than one channel through the stem, such as when two fluids are to be delivered to the bristles and the fluids are not compatible if mixed together. In such a case, manufacturing requirements for the stem mold results in the stem being fairly large in diameter, bulky and unattractive.

It would be desirable to have a toothbrush stem which accommodates more than one fluid channel, while being relatively slim and attractive.

SUMMARY OF THE INVENTION

Accordingly, the present invention is a stem portion for a toothbrush for delivering fluid supplied from at least one reservoir to at least one exit opening in a bristle plate with bristles, comprising: a stem body having an interior longitudinal opening; and a core member configured to fit within the stem body opening, wherein the stem body and/or the core member have at least one groove extending therealong, wherein said at least one groove receives fluid at one end of the stem portion and delivers fluid to the bristle plate opening.

BEST MODE FOR CARRYING OUT THE INVENTION

Figure 1:
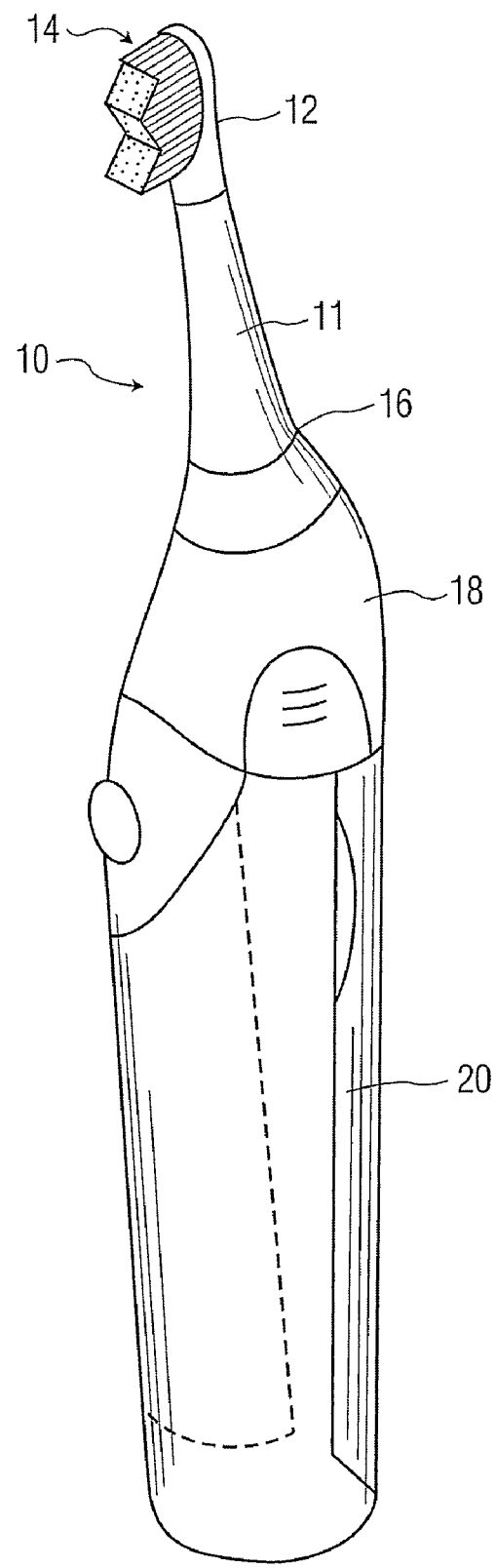
FIG. 1 is a perspective view of a power toothbrush which includes the toothbrush stem of the present invention.
Figure 2:
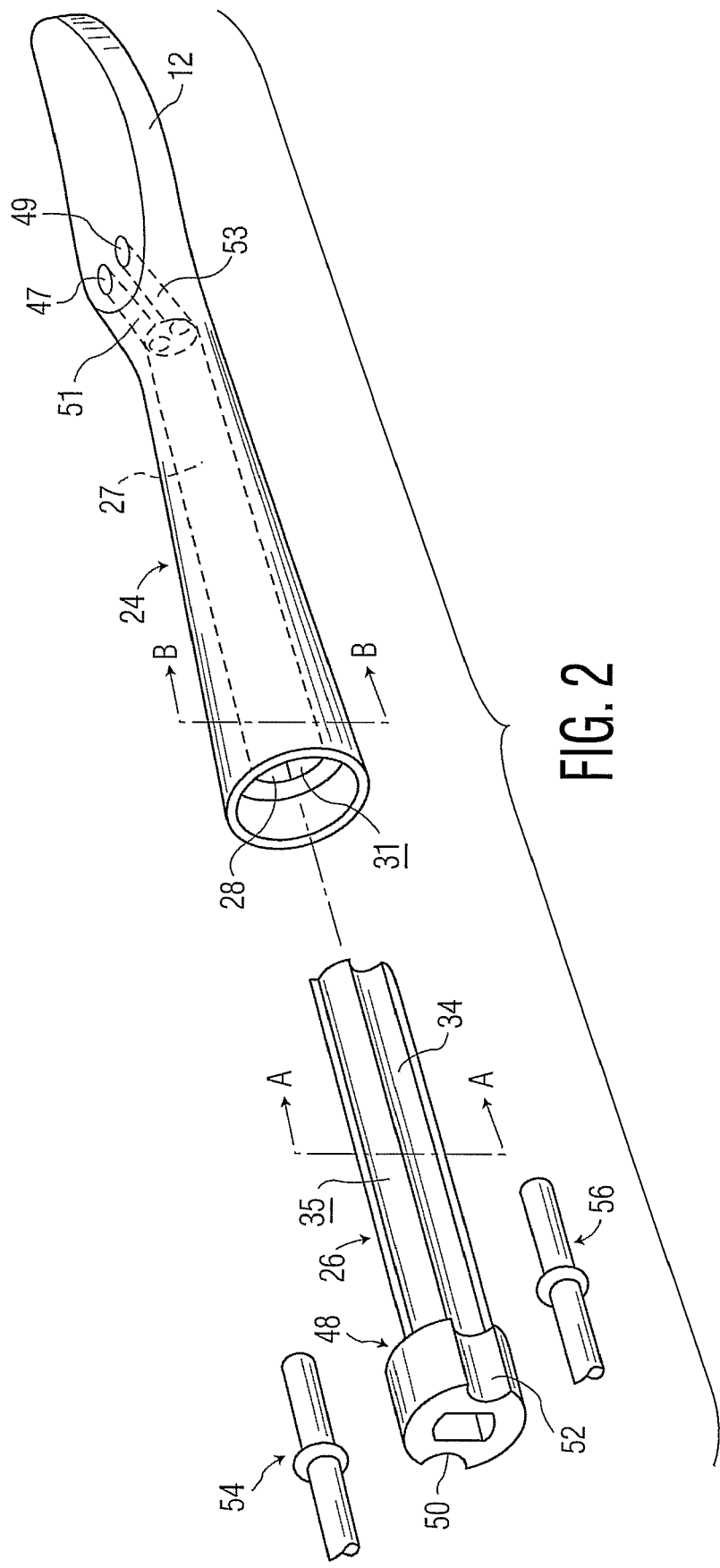
FIG. 2 is an exploded view of one embodiment of the toothbrush stem of the present invention.
Figure 3:
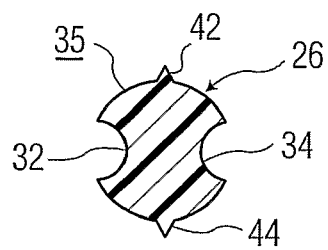
FIG. 3 is a cross-sectional view of the toothbrush stem of FIG. 2 taken along lines A-A of FIG. 2.
Figure 4:
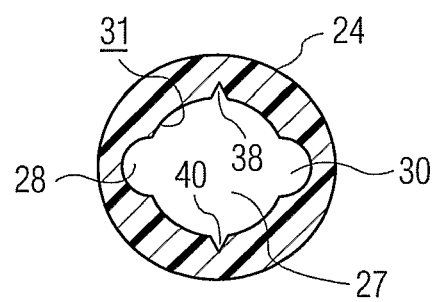
FIG. 4 is a cross-sectional view of the toothbrush stem of FIG. 2 taken along lines B-B of FIG. 2.

FIGS. 1 and 2 show the toothbrush stem of the present invention in a toothbrush 10. The toothbrush stem, shown generally at 11, terminates in a brush plate 12 from which toothbrush bristles extend, forming a bristle field 14 for the toothbrush. Brush plate 12 can either be in the form of a continuous extension of stem 11 as shown in FIG. 1, or it can be a separate piece which is attached to the forward end of the stem. The rear, i.e. distal, end 16 of stem 11 connects to a head portion 18 of a toothbrush, which in turn is connected, usually removably, to a handle portion 20.

The particular arrangement and configuration of the head portion 18 and the handle portion 20 of a toothbrush are shown for convenience and illustration, and it should be understood that those portions of the toothbrush can take many different arrangements and configurations relative to the toothbrush stem 11.

The toothbrush stem 11 includes a shell portion or stem body 24 and a core portion 26. The shell portion 24 is hollow and adapted to receive core portion 26 therein. Both the shell portion and the core portion are typically made from plastic, although other materials can be used. The hollow opening 27 in shell portion 24, which extends longitudinally through the shell, is generally circular in cross-section, with two semi-circular grooves 28 and 30 in the interior surface 31 thereof which extend for the length of the shell 24, as shown in FIG. 2. Typically, grooves 28 and 30 oppose each other, spaced apart by 180°, although different angular placements are possible.

Core portion 26 is also generally circular in cross-section except for two semi-circular grooves 32 and 34 in the outer surface 35 of the core portion. Grooves 28, 30, 32 and 34 are arranged and spaced in the embodiment shown so that grooves 28 and 30 align with grooves 32 and 34 to define approximately circular channels which extend the length of the stem. In alternative arrangements, the grooves in the shell portion or the core portion could be eliminated, leaving a groove or grooves in one portion only, or there could be one groove in the shell portion and another non-aligned groove in the core portion. Further, there could be only one pair of aligned grooves or more than two. Further, the grooves could be other cross-sectional shapes than semi-circular, e.g. elliptical, half-square, etc.

In the embodiment shown, the core portion has an outside diameter of approximately 4 mm, with a ½ mm semi-circular groove in the outer surface thereof. The internal diameter of the shell 24 is slightly greater than 4 mm, allowing the core to fit conveniently into the shell. The grooves in the internal surface of the core also have an approximately ½ mm radius. These dimensions, however, can change depending upon the particular application. In the embodiment shown, the outside diameter of the shell will vary slightly, to give a tapered, attractive appearance, from approximately 7 mm at the distal end to 6 mm at the brush end. These dimensions, however, can also be varied.

Shell portion 24 will also typically include two opposed small key slots 38 and 40 in the interior surface 31 thereof. Key slots 38 and 40 will generally oppose each other, extending substantially the length of the shell, and will usually be positioned at 90° relative to grooves 28 and 30 in the shell portion.

The core portion 26 has mating rib elements 42 and 44 which extend outwardly from the exterior surface 15 thereof. Rib elements 42 and 44 are configured and arranged to fit within key slots 38 and 40. The ribs 42 and 44 are crushable to form a fluid-tight barrier between the opposing sets of mating grooves/ribs. Welding can also be used to form a fluid-tight barrier, in which case slots 38 and 40 are not necessary.

This arrangement permits two paths for fluids through the stem 11 of the toothbrush. At the brushhead end of stem 11, the two channels can be extended through the bristle plate 12 to selected exit points 47, 49 in the bristle plate. The fluid pathways 51, 53 through the bristle plate are typically molded into the bristle plate 12. They can, however, be in the form of small tubes in a hollow bristle plate.

At the distal end of core portion 26 is a coupling member 48 which is slightly larger than the external diameter of the core portion. For instance, for a core portion having an outside diameter of 4 mm, the outside diameter of coupling member 48 can be approximately 5 mm. Coupling member 48 includes grooves 50 and 52 which mate with the sets of grooves in the shell and core portions. Coupling member 48 is adapted to form a fluid-tight barrier with a mating surface of shell 24, either by a friction fit or other means.

Grooves 50 and 52 are adapted to receive the ends of fluid tubes 54 and 56 which extend from fluid reservoir(s) in another part of the toothbrush, such as handle 20. There could be separate reservoirs for the two channels, or a single reservoir. Tubes 54 and 56 snap into place in the coupling member before the entire core portion 26 is positioned within shell 24. Adhesive or other means is used to ensure a fluid-tight coupling between tubes 54 and 56 and coupling member 48.

In operation, fluids are pumped from the reservoir(s) through tubes 54 and 56 into the channels in stem 11 formed by the semi-circular grooves 28 and 30 in the shell portion and aligned grooves 32 and 34 in the core portion.

The above arrangement provides a multi-channel capability in the toothbrush stem for fluid dispensing while maintaining the stem relatively slim and attractive during the molding process. While the embodiment shown includes two fluid channels in stem 11, it should be understood that the principles of the present invention extend to an arrangement as indicated above with only a single channel and, further, more than two channels, depending on the particular application/requirement.

Figure 5:
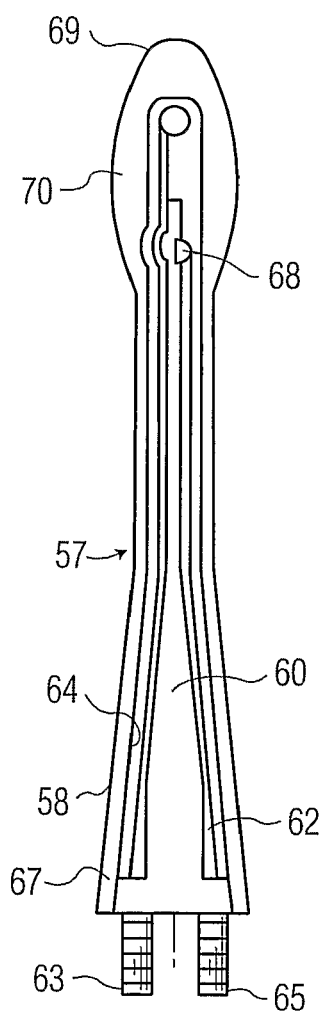
FIG. 5 is a view of a second embodiment of the toothbrush stem of the present invention, showing the back of the toothbrush stem and adjoining bristle plate.

FIG. 5 shows a back view of another embodiment of a stem 57 of the present invention. This embodiment includes a lower longitudinal half portion 58 and an upper longitudinal half portion 60 which are secured together. The internal surfaces of the two portions 58 and 60 are configured to form two separate channels when secured together. The channels 62, 64 begin at an entry point at the distal end 67 of the stem, which includes hollow entry members 63 and 65. The two channels basically are arranged side-by-side, angling somewhat toward each other as the outside diameter of stem 57 decreases along its length. The entry members 63 and 65 connect with the channels 62, 64. The channels defined in this embodiment are more irregular in configuration than the channels in the embodiment of FIG. 1. One channel 62 extends along the stem to a first exit opening 68 in bristle plate 69.

Typically, a valve, such as a duckbill valve (not shown), is positioned in said opening. Fluid then moves through channel 62 through opening 68 in the bristle plate and the valve into the bristle field. The other channel 64 extends generally along the opposite side of the stem in the same horizontal plane and includes a channel portion which extends beyond exit opening 68 for the first channel to a second exit opening 70 spaced apart from opening 68, toward the other end of the bristle plate 69. Again, in this embodiment, a single channel could be provided through the stem or more than two channels.

Although a preferred embodiment of the invention has been disclosed for purposes of illustration, it should be understood that various changes, modifications and substitutions may be incorporated without departing from the spirit of the invention, which is defined by the claims which follow.

The invention claimed is:

1. A stem portion for a toothbrush for delivering fluid supplied from at least one reservoir to at least one exit opening in a bristle plate with bristles, comprising:
   a stem body having an interior longitudinal opening, the stem body having an outer surface and inner surface which defines the longitudinal opening, wherein the stem body terminates in a bristle plate with bristles which is integral with the stem body or attached thereto; and
   a core member configured to fit within the stem body opening, wherein a rear end of the stem portion connects to the remainder of the toothbrush, the stem body having an outer surface, wherein the stem body and the core member each have at least two grooves along the lengths thereof, the core member including an outer surface which extends between the grooves therein, wherein one groove in an inner surface of the stem body which opens onto the inner surface of the stem body and one mating groove in the outer surface of the core member, form a first stem channel, and wherein a second groove in the inner surface of the stem body, which opens onto the inner surface of the stem body and a second mating groove in the outer surface of the core member form a second stem channel, wherein the first and second stem channels extend to the bristle plate, for delivery of fluids to the bristle plate, and wherein the core member includes two rib elements which extend outwardly from said outer surface of the core member and are located, respectively, between the first and second stem channels, contacting the stem body in such a manner to provide a fluid-tight relationship between the stem body and the core member, separating the fluids in the first and second stem channels along the lengths thereof.

2. The stem portion of claim 1, wherein the core member includes a coupling element at a distal end thereof, which includes grooved portions which communicate with the first and second channels in the stem body and which are adapted to receive fluid pathway channels from the reservoir.

3. The stem portion of claim 1, wherein the bristle plate includes fluid pathway portions which extend from the first and second channels in the stem portion to exit openings in the bristle plate, permitting fluid to move therethrough to the bristles.

4. The stem portion of claim 1, wherein the first and second channels are opposed, approximately 180° apart.

5. The stem portion of claim 1, wherein the extending elements are crushable ribs and the stem body includes two mating key slots, providing a fluid-tight relationship between the stem body and the core member, separating the first and second channels.

6. The stem portion of claim 1, wherein the extending elements are ribs and the stem body includes two mating key slots, providing a friction-fit fluid-tight relationship between the stem body and the core member, separating the first and second channels.

7. The stem portion of claim 1, wherein the two extending elements are ribs which are welded to the stem body to provide a fluid-tight relationship between the stem body and the core member, separating the first and second channels.

8. The stem portion of claim 1, wherein the first and second channels are approximately circular.

9. The stem portion of claim 1, wherein one channel extends to one exit opening in the bristle plate and the other channel extends to another exit opening in the bristle plate.

10. A stem portion for a toothbrush for delivering fluid supplied from at least one reservoir to at least one exit opening in a bristle plate with bristles, comprising:

a stem body portion having a hollow interior; and a stem core portion adapted to be fitted within the stem body portion in a fluid-tight relationship, wherein an inner surface of the stem body portion and an outer surface of the stem core portion both have grooves therein which are configured to mate together to define two fluid-tight separate channels therealong, extending to the bristle plate, for delivery of fluid to said bristle plate, wherein the inner surface of the stem body portion and the outer surface of the stem core portion include surface portions which extend between the grooves therein, wherein one of the stem core portion and the stem body portion includes two rib elements which extend from the surface portions thereof, between the first and second channels, contacting the other of the stem core portion and the stem body portion in such a manner to provide a fluid-tight relationship between the stem core portion and the stem body portion, separating the fluids in the separate channels along the length thereof.

11. The stem portion of claim 10, wherein one channel extends to one opening in the bristle plate and the other channel extends to a second opening in the bristle plate.

* * * * *